(12) United States Patent
O'Neil

(10) Patent No.: US 7,105,043 B2
(45) Date of Patent: Sep. 12, 2006

(54) SEALING MECHANISM FOR GAS CHROMATOGRAPH MACHINES

(76) Inventor: Gregory Gerard O'Neil, 1672 Bird Rd., Independence, KY (US) 41051

( * ) Notice: Subject to any disclaimer, the term of this patent is extended or adjusted under 35 U.S.C. 154(b) by 410 days.

(21) Appl. No.: 10/677,741

(22) Filed: Oct. 3, 2003

(65) Prior Publication Data
US 2005/0074367 A1   Apr. 7, 2005

(51) Int. Cl.
*B01D 53/02* (2006.01)

(52) U.S. Cl. ............... 96/101; 96/105; 73/864.66; 277/312

(58) Field of Classification Search ............ 96/101, 96/105, 106; 422/103; 73/23.41, 23.42, 73/864.86; 277/312
See application file for complete search history.

(56) References Cited

U.S. PATENT DOCUMENTS 3,939,713 A * 2/1976 Estey ................ 73/864.86
4,079,009 A * 3/1978 Seiler et al. ........... 210/198.2

FOREIGN PATENT DOCUMENTS

JP          2003344374 A  * 12/2003

* cited by examiner

*Primary Examiner*—Robert A. Hopkins
(74) *Attorney, Agent, or Firm*—Stites & Harbison PLLC; Ross F. Hunt, Jr.

(57) ABSTRACT

A sealing mechanism for a gas chromatograph machine includes a weldment attachment mountable at the weldment assembly of the machine. The attachment has a passage therethrough for gas communicated to the weldment assembly. An actuator imparts a direct force on the weldment attachment to move it linearly towards an injection port of the machine and to sealingly clamp the weldment attachment onto the port. Torsional forces are not applied on the weldment attachment by the actuator.

39 Claims, 5 Drawing Sheets

SEALING MECHANISM FOR GAS CHROMATOGRAPH MACHINES

This invention relates to a mechanism used for sealing two sealing halves in a gas chromatograph machine and specifically for sealing the injection port of a gas chromatograph machine.

BACKGROUND OF THE INVENTION

Gas chromatography is a technique used for the separation of mixtures. In gas chromatography, the sample is often introduced as a liquid into the injection port whereafter it is volatilized. An inert gas is used as a carrier to propel the volatilized sample into the gas chromatographic column where the sample mixture is separated into its components. Each separated component is further propelled by the carrier gas through the exit of the gas chromatographic column into a detector. The detector then provides information regarding the amount and identity of each component of the sample mixture.

The injection port is the point at which the sample is introduced into the machine prior to separation of components. The injection port typically operates at elevated temperatures to ensure that the sample mixture is vaporized and transitions into the gas phase prior to separation entry to the chromatographic column. To assist this vaporization a disposable liner made of an inert material such as glass or quartz is placed within the injection port. A side effect of this process is that the liner also traps non-volatile components within the sample mixture. After repeated exposure to sample introductions, the injection port liner may loose its inert characteristics or become dirty and thus require replacement.

When using dirty sample matrices liner replacement is required frequently. This requires the uncoupling of two sealing surfaces to remove and replace the liner, followed by a recoupling of these sealing surfaces. This sealing is usually provided through the compression of an o-ring or ferrule around the outer diameter of the liner and positioned between the two sealing halves of the injection port body.

The normal way of forming this compression is through the use of a threaded weldment nut assembly onto an injection port body which contains a sealing bevel and metal tube to house the injection port liner. Such an arrangement is illustrated in FIG. 1. Components of the threaded nut assembly usually include gas introduction lines connected to a sealing septum to bring the carrier gas to the inlet. Once the weldment assembly is removed a liner and seal is placed into the injection port body. The threaded weldment nut is then turned onto matching threads on the injection port body producing a compression seal on an O-ring around the outer diameter of the injection port liner. This compression seal couples the liner and allows the flow of carrier gas supply through the liner into the gas chromatographic column.

The threaded weldment nut assembly often requires tools such as a wrench to rotate the nut onto the thread of the injection port body. The weldment nut is inductively heated when it is in contact with the injection port body, resulting in it often being too hot to handle (temperatures up to 350° C.). When removing the weldment nut from the injection port body it must be turned several times, often with a wrench, before it is released from the injection port body. After replacing the old liner, the threaded weldment nut is cool and thus exhibits difficulty in rethreading onto the thread of the hot injection port body. This can result in cross threading and seal leakage. Liner seals may also be damaged and leak due to torsional forces produced by rotating the weldment nut.

Additionally, this process of replacing the liner may be dangerous for operators if their hands contact the hot components of the injection port body which can easily occur when rotating the weldment nut assembly. The process of unthreading and rethreading may take several minutes to accomplish which can have deleterious effects on the system by exposing the gas chromatograph and column to air.

The present invention seeks to improve the ease and efficiency of removing and replacing the weldment assembly and on the whole making it safer for operators to use.

SUMMARY OF THE INVENTION

In one embodiment the invention is a sealing mechanism for a gas chromatograph machine comprising:

a weldment attachment mountable at the weldment assembly of a gas chromatograph machine and having a passage therethrough for gas communicated to the weldment assembly; and actuating means for actuating a direct force on the weldment attachment to linearly move it towards an injection port of the gas chromatograph machine and sealingly clamp the weldment attachment onto the injection port, wherein the actuating means does not apply torsional forces on the weldment attachment.

In another embodiment the invention is sealing mechanism for a gas chromatograph machine comprising:

an annular base mountable at the weldment assembly of a gas chromatograph machine, the base having a passage therethrough for gas communicated to the weldment assembly;

a lever pivotally connected to the annular base and pivotally attached to an injection port of the gas chromatograph machine, wherein the base is adapted to be seated on top of the injection port and sealed against thereto by pivotally moving the lever to apply a direct force and clamp the base onto the injection port.

In still another embodiment the invention is a sealing mechanism for a gas chromatograph machine comprising:

an annular base mountable on the inlet weldment assembly of a gas chromatograph machine, the base providing a passage therethrough for gas;

a latch having two arms pivotally connected on opposing sides on the exterior circumference of the annular base, the arms being provided with hinging means to hingedly attach the latch to a corresponding attachment on an injection port of the machine, the base being mountable on the injection port, wherein the latch is pivotally levered against the injection port to directly clamp the base onto the injection port in sealing engagement and without imparting torsional force on the base.

In yet another embodiment the invention is a method of sealing a weldment assembly and an injection port on a gas chromatograph machine including:

mounting a weldment assembly onto the injection port, wherein the weldment assembly includes a latch having two arms and is pivotally connected to opposite sides of the exterior circumference of an annular base, the arms having coupling means for coupling with complementary means located at the injection port in order to mount the latch onto the injection port; and pivotally levering the latch at the coupling to clamp the base down onto the injection port.

In still another embodiment the invention is a method of sealing a weldment assembly and an injection port on a gas chromatograph machine including:

mounting a weldment attachment at the weldment assembly, the weldment attachment providing a passage therethrough for gas communicated to the weldment assembly;

actuating an actuating means connected to the weldment attachment, and thereby applying a direct force on the weldment attachment moving it towards the injection port and sealingly clamping the weldment attachment against the injection port, wherein torsional forces are not applied on the weldment attachment by the actuating means.

BRIEF DESCRIPTION OF THE DRAWINGS

The present invention is described further by way of example with reference to the accompanying drawings of which.

DETAILED DESCRIPTION OF THE INVENTION

Figure 1:
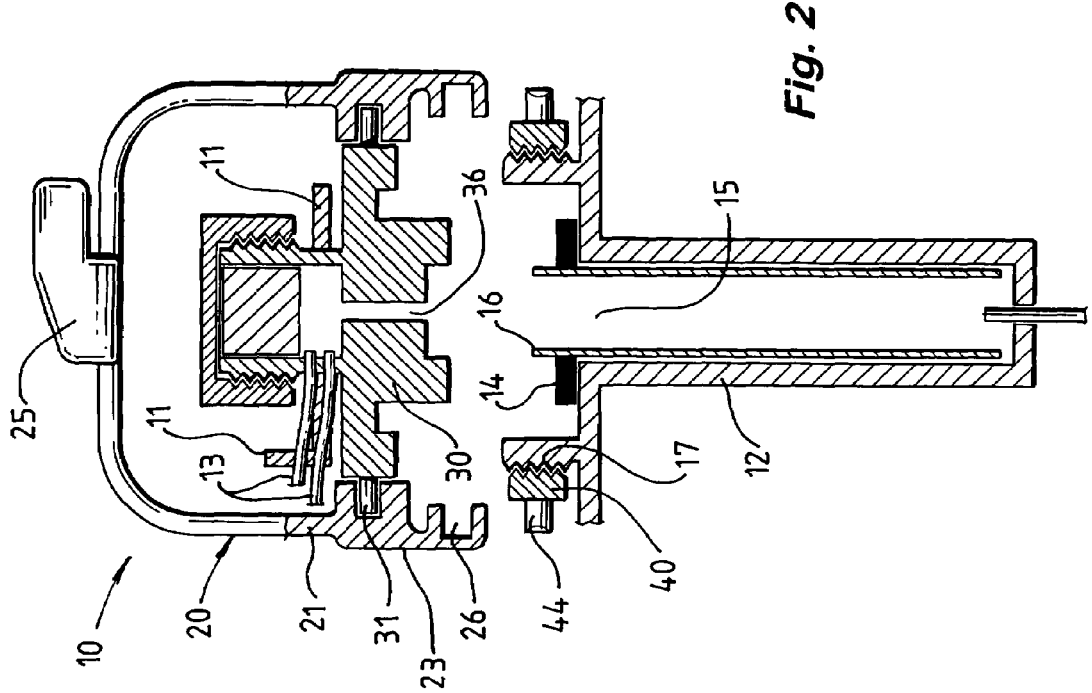
FIG. 1 is a schematic side view of an injection port of a gas chromatograph machine sealed using a known assembly.

FIG. 1 illustrates a known device for sealing an injection port body of a gas chromatograph machine. A weldment frame 11 including a sealing septum 18 and septum nut 19 carries an internally threaded weldment nut A that is screwed onto a corresponding thread 17 on the injection port body 12. Gas lines 13 connected to the weldment frame 11 are for communicating carrier gas to the weldment frame 11 the on to the injection port inlet 15 when sealed.

In the following a preferred embodiment of a sealing mechanism of a gas chromatograph machine is described in detail. Essentially, sealing mechanism avoids the use of a thread to screw the weldment frame 11 onto an O-ring 14 of the injection port body 12. Instead the mechanism uses a clamping force to form a tight and even seal between the injection port body and weldment frame. Accordingly, the present sealing mechanism eliminates any torsional forces involved in sealing the injection port and instead applies a direct force normal to the mouth of the injection port inlet 15 to create a direct and balanced seal. With this mechanism there is little chance of misalignment and damage or leakage caused by incorrect sealing.

The preferred embodiment of the sealing mechanism employs a lever system to achieve a direct clamping force. However, it is understood that other mechanisms are also able to provide the necessary direct force to seal the injection port of a gas chromatograph and these are also described briefly below as alternate embodiments of the invention.

Figure 2:
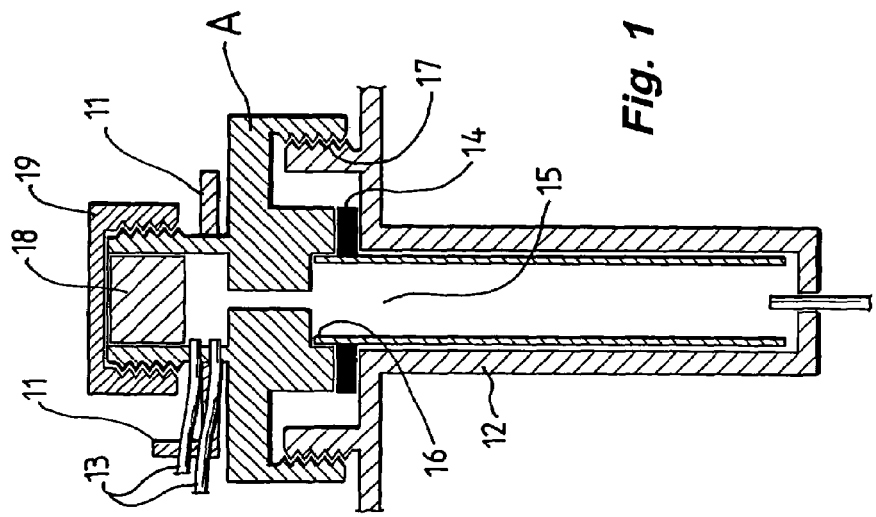
FIG. 2 is a side schematic view of an injection port of a gas chromatograph machine prior to sealed using a sealing mechanism according to one embodiment of the present invention.

FIG. 2 illustrates a sealing mechanism 10 spaced above injection port body 12 before mounting. The sealing mechanism employs a lever style configuration to apply a direct downward force to clamp weldment frame 11 to injection port body 12. The sealing mechanism 10 incorporates weldment frame 11 and the gas lines 13 connected thereto to form a weldment assembly capable of being sealingly mounted onto the injection port body by way of a clamping force.

In this embodiment, the sealing mechanism 10 includes a base ring 30 adapted to fit onto the underside of weldment frame 11 such that the gas lines communicate carrier gas through the weldment frame 11 and through a central flow aperture 36 of base ring 30, which in turn is designed to be sealingly connected to inlet port 15 in the injection port body.

Latch 20 is hinged to opposing sides of base ring 30 and in use is levered down to provide the clamping force for sealing.

Figure 3:
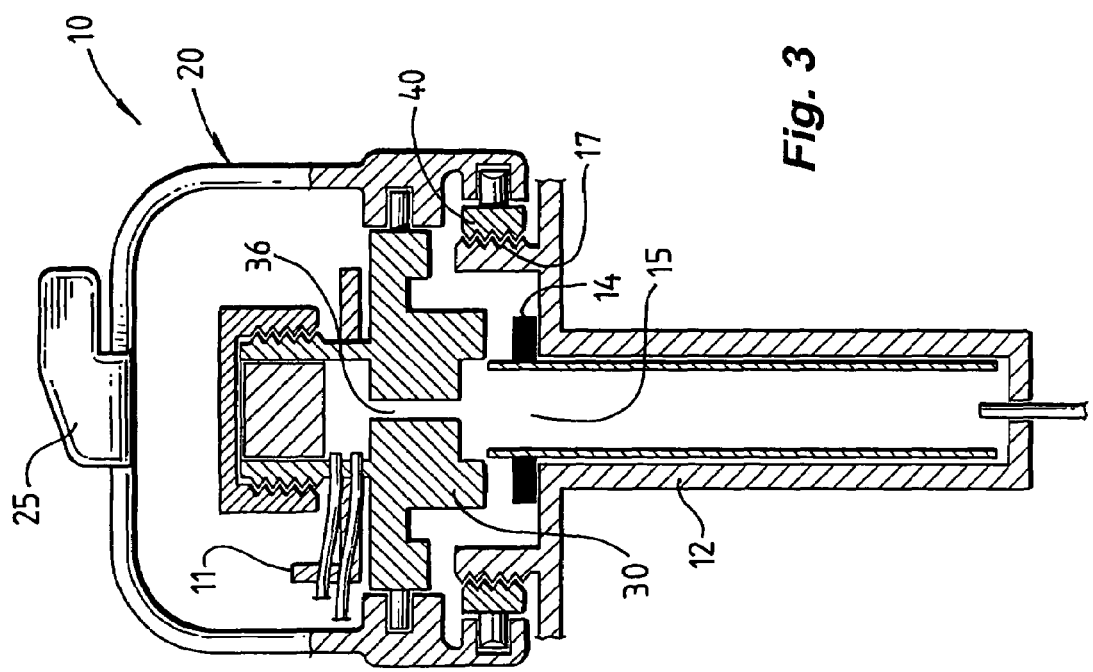
FIG. 3 is a view similar to FIG. 2 but showing the mechanism mounted on the injection port in an unlocked position.

FIG. 2 schematically illustrates latch 20 pivoted to opposite sides of base ring 30. To seal the injection port body the whole weldment assembly 10 is brought down and centered on the inlet port 15 as illustrated in FIG. 3. Base ring 30 is mounted over O-ring 14 to prepare for sealing. Latch 20 is then levered down to the position illustrated in FIG. 4 thereby bringing base ring 30 and O-ring 14 close in contact to seal the injection port body.

To retrofit the present sealing mechanism 10 to existing gas chromatograph systems some form of an adapter is required as an engagement means for latch 20. In the present embodiment latch 20 is unable to properly engage with thread 17. Accordingly, adapter ring 40 is fitted onto the existing external thread 17 and the latch engages this adapter. The adapter enables existing gas chromatograph machines to operate with the present sealing mechanism. Specifically, the adapter is screwed onto the existing thread 17 and sits on a seat surrounding inlet port 15.

Figure 4:
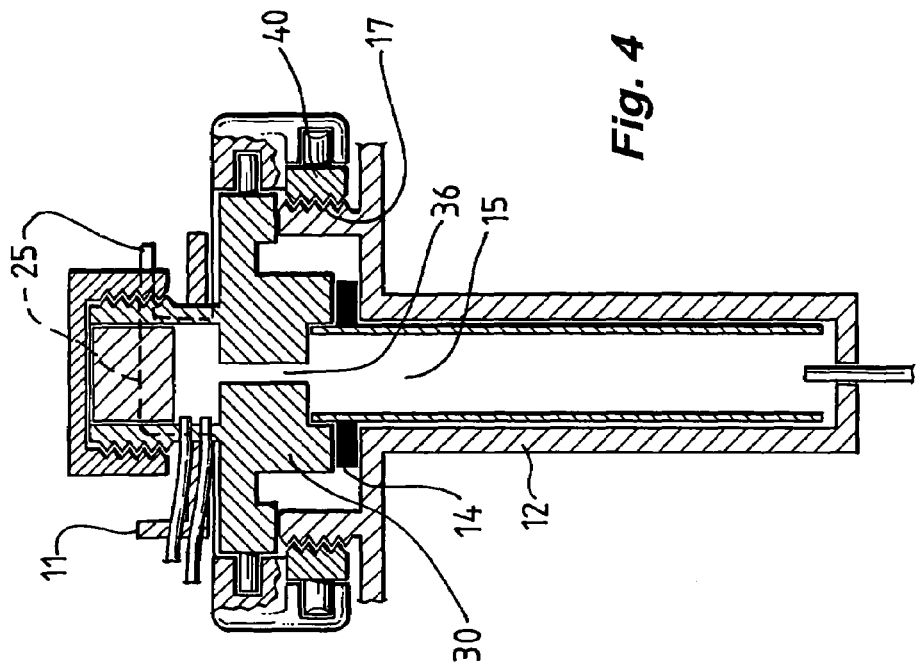
FIG. 4 is a view similar to FIG. 3 but showing the mechanism in the locked position.

FIGS. 2 to 4 schematically illustrate the adapter ring which has an internal thread that cooperates with external thread 17 and an exterior circumference onto which latch 20 can be anchored and levered down.

Figure 5:
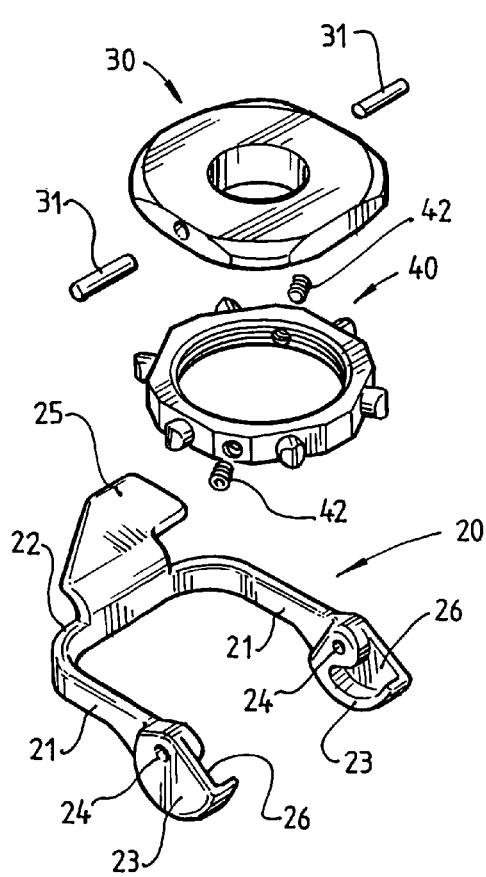
FIG. 5 is an exploded perspective view of one embodiment of the sealing mechanism.

FIG. 5 illustrates in an exploded format the various components defining the preferred sealing mechanism 10, namely latch 20, base ring 30 with lugs 31, and adapter ring 40.

Figure 6:
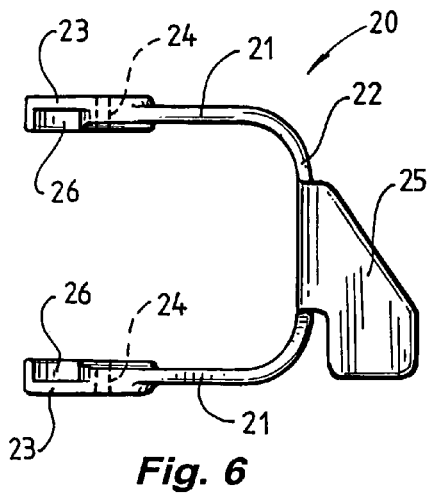
FIG. 6 is a plan view of a latch used in the first embodiment of the sealing mechanism.
Figure 7:
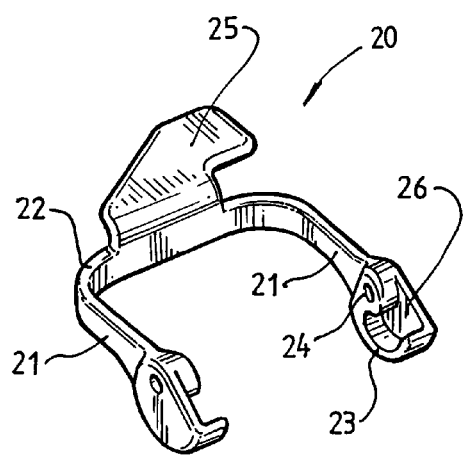
FIG. 7 is a perspective view of the latch of FIG. 6.

Latch 20 is illustrated in FIGS. 6 and 7 and is substantially U-shaped and has a central portion 22 from which two side arms 21 extend in opposite directions bending through approximately 90° to terminate in broad flanges 23, which face each other. Flanges 23 have a cambered profile and are each provided with a small aperture 24 designed to receive lugs 31 extending from opposite side edges 32 of base ring 30.

This connection provides a hinged pivoting relationship between latch 20 and base ring 30.

Central portion 22 of latch 20 is provided with an upstanding lever handle 25 which is used by an operator to, in use, take a hold of the latch to pull down and seal the injection port.

Figure 8:
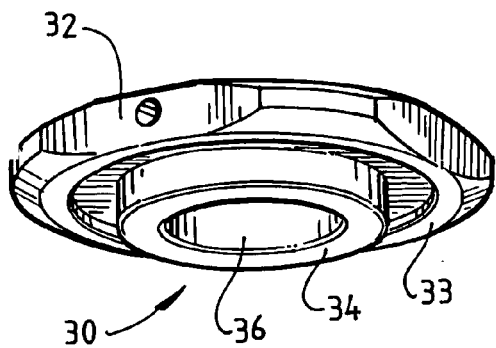
FIG. 8 is a perspective view of a base ring used in the first embodiment of the sealing mechanism.
Figure 9:
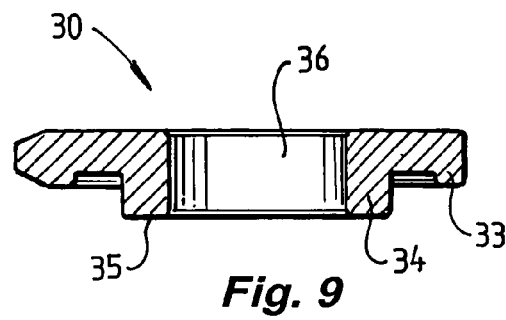
FIG. 9 is a side sectional view of the base ring of FIG. 8.

Base ring 30 as illustrated in FIGS. 8 and 9 is annular in shape and can be round, hexagonal or similar. Base ring 30 is substantially defined by a large ring 33 and an adjacent concentric small ring 34. Flow aperture 36 is located along the axial center of the base ring. Small ring 34 acts as a spacer and complementarily communicates with the port 15 of injection port body 12. The annular bottom edge 35 of small ring 34 contacts against the O-ring 14 located around the inlet port 15 on the injection port body 12 to form a seal. The underside of large ring 33 adjacent small ring 34 defines one of the clamping surfaces used in sealing the weldment frame to the injection port body.

Figure 10:
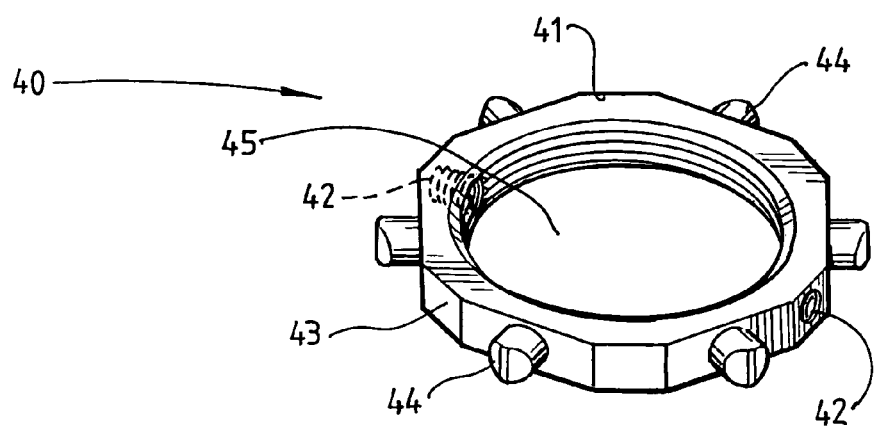
FIG. 10 is a perspective view of an adapter ring used in the first embodiment of the sealing mechanism.
Figure 11:
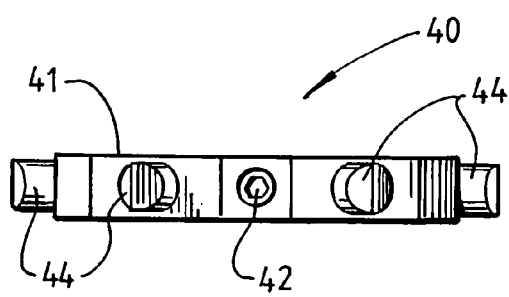
FIG. 11 is a side view of the adapter ring of FIG. 10.

The other clamping surface to which the large ring 33 clamps is an upper annular edge 41 of the adapter ring 40. Adapter ring 40 is illustrated in FIGS. 10 and 11 and is an annular ring having an internal thread for cooperating with existing thread 17, and a series of pins 44 provided on the exterior circumference extending radially outward. Once adapter ring 40 is screwed onto thread 17 at injection port inlet 15, grub screws 42 radially located on opposite sides of body 43 of adapter ring 40 adjust and secure the position of adapter ring 40 with respect to the annular upstanding lip 16 of the injection inlet port 15. The grub screws when tightened protrude through the inner circumference of adapter ring 40 and into the centre 45 of the ring. The screws are tightened by way of a hex-wrench which end locates in a corresponding grub screw aperture located on the exterior circumference of ring 40. As the grub screws are tightened they extend through to the inner circumference of adapter ring 40 and engage with external thread 17.

On the exterior circumference of adapter ring 40 each pin 44 has a paired pin on a directly opposite point of the exterior circumference. In other words the paired pins are spaced 180° on the exterior circumference. Latch 20 is designed to hook onto one of the pair of pins 44 on the adapter ring 40. The pair of pins 44 acts as the fulcrum or pivoting point for the latch 20 so that the latch can be levered down to seal the weldment assembly onto the injection port body 12.

As illustrated in FIGS. 6 and 7, each flange 23 on side arms 21 has a shaped recess 26 on an interior face of the flange such that the shaped recesses 26 on the two flanges face one another. The shaped recesses 26 are each adapted to receive one pin 44 in a pair. The shape of the recesses 26 is bent at an angle so that pins extending into the recesses are made to follow the shape from one end of the recess to the other.

Figure 12:
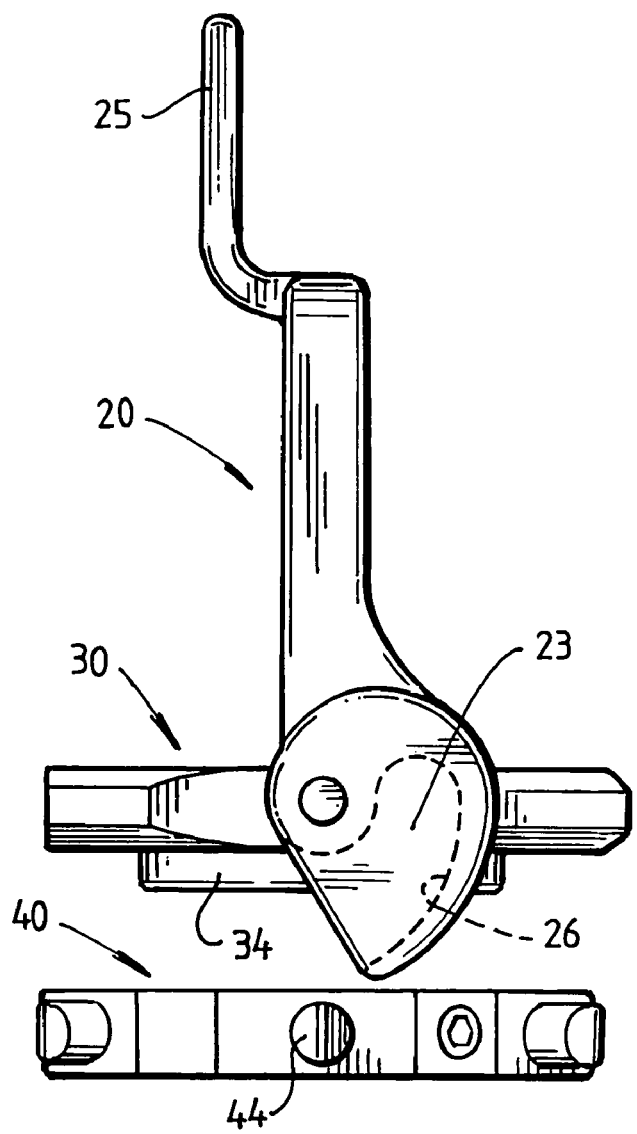
FIG. 12 is a side view of a sealing mechanism in the locked position.

In use where the latch and base ring arrangement are mounted over the adapter ring with opposing pins 44 extending into the recesses 26, pivoting movement of latch 20 moves the hinged joint at lugs 31 and consequently base ring 30, directly over injection port 15 and down onto the port in a manner that clamps the base ring on top of the adapter ring. In the unsealed position latch 20 is substantially upright over the injection port body. This position can be seen in FIG. 12. From here the latch, base ring and rest of the weldment assembly, is mounted on the inlet port and the latch levered down to a substantially horizontal position to scoop around and clamp the base ring and hence weldment assembly, onto the adapter ring and injection port body.

Figure 13:
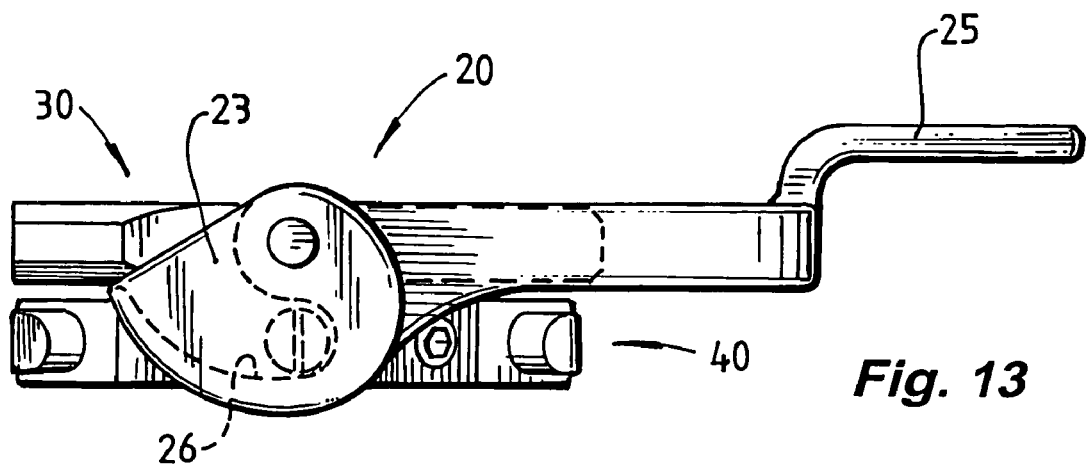
FIG. 13 is the same view as FIG. 12 but showing the sealing mechanism in the locked position.

The sealing mechanism is illustrated in FIG. 13 in the sealed position (the injection port body and part of the weldment assembly are not shown). The hinged joint at lugs 31 between latch 20 and base 30 is located sufficiently close to the shaped recess such that as the latch is pulled down, the hinged joint moves in a path around the recess terminating at a point lower than where it began.

The cambered profile of the flanges 23 assist in smooth rotation of the latch arm by providing a cam surface acting as a support against an upper surface of the injection port.

Accordingly, a tight seal is produced between the injection port body and weldment assembly. As there is no need for any turning movement on threads, the seal is formed with an even distribution of pressure around the base ring and adapter ring and is devoid of any misalignment or uneven forces that may be produced by the torsional forces involved in screwing a component on a thread. The compression created on the sealing O-ring is direct. Furthermore, the only tool required is a small hex-wrench; there is no need for the snap ring pliers and other tools required for assembling and disassembling known seals. The assembling and disassembling process is faster than that for known systems and the danger of injury to the operator is greatly reduced as direct contact with the hot injection port body is minimised.

In threading the adapter ring on the injection inlet port the alignment of pins against the latch arms may not initially be correct. In this case the adapter ring can be rotated slightly to one side or the other until the latching arms align properly on the pins and the lever moves smoothly and firmly to clamp down the weldment assembly.

The above embodiment describes a sealing mechanism used on existing gas chromatograph machines. Other embodiments are also possible. For example, where there is a possibility of providing this sealing mechanism on new machines, there would be no need for an external thread 17. Lip 16 of the inlet port could be designed to cooperate directly with the latch without the need for an adapter ring.

Alternatively external thread 17 may remain and instead the configuration of latch arms 21 could be changed in design to directly engage with external thread 17 while still allowing the latch to apply a downward clamping force. More specifically, the recesses inside arms 21 could be designed to fit onto, and lever from, part of the external thread 17 at the inlet 15 of the injection port body.

In another embodiment of the sealing mechanism a device could be provided having a multi-pivoting hinge attached to one side of the injection port body. The hinge would be moveable in two or three dimensional planes. The device on a second side would be provided with a lock down clip or lever so that the device could be used to apply non-torsional pressure to the sealing surface and locked once sealed.

A simplified version of the sealing mechanism would not use shaped recesses for pivoting but a simple hinge that would still allow the latch to be pulled down and lifted up without any torsional force.

In still an alternate embodiment the necessary direct pressure required to seal the two surfaces could be applied using pneumatic or hydraulic means. This may, for example, involve pneumatic pressure from an external compressed supply used in connection with the weldment assembly to sealingly force it onto the O-ring. The actuator could, for example, be a pneumatic ram mounted on a frame supported by the injection port body. A lock means would ensure that the sealing engagement is retained.

A two way valve in the pneumatic line would dictate in which direction the pneumatic force is to be provided, namely whether to seal or unseal the injection port. Hydraulic means would operate in a similar manner.

In a further embodiment the non-torsional direct force could be applied using magnetic attraction. Traditional magnets or electromagnetic devices could be used to form an attraction between the weldment assembly and the inlet port to firmly seal the two together. In the case of electromagnetic instruments, magnetic attraction may be used locate and create the initial seal and a regular locking device used to maintain the seal.

The invention claimed is:

1. A sealing mechanism for a gas chromatograph machine comprising:
   a weldment attachment mountable at the weldment assembly of a gas chromatograph machine and having a passage therethrough for gas communicated to the weldment assembly; and
   actuating means for actuating a direct force on the weldment attachment to linearly move it towards an injection port of the gas chromatograph machine and sealingly clamp the weldment attachment onto the injection port, wherein the actuating means does not apply torsional forces on the weldment attachment.

2. The sealing mechanism claimed in claim 1, wherein the actuating means is a hinged lever.

3. The sealing mechanism claimed in claim 2, wherein the lever is attachable to and leverable against an external thread at the inlet of the injection port, the lever further having retaining means to retain the lever in a sealed position.

4. The sealing mechanism claimed in claim 2, wherein the lever is hinged to the injection port and has retaining means to retain the lever in a sealed position.

5. The sealing mechanism claimed in claim 2, wherein the hinge on the hinged lever is a multi-pivoting hinge.

6. The sealing mechanism claimed in claim 2, wherein the lever is a latch having two arms pivotably connected to opposing sides of the weldment attachment, the arms being provided with channels on inner faces thereof.

7. The sealing mechanism claimed in claim 6, wherein the channels engage with corresponding protrusions at the injection port such that the pivoting latch is pivotably levered on the protrusions to clamp the weldment attachment onto the injection port.

8. The sealing mechanism claimed in claim 7, wherein the channels are a curved shape such that, during levering, the protrusions follow a curved path in the channels that will cause the weldment attachment to pull down onto the injection port to seal the port.

9. The sealing mechanism claimed in claim 6, wherein the latch has a handle.

10. The sealing mechanism claimed in claim 6, wherein the latch arms terminate in flanges having a cambered edge that, in use, provide a cam surface against the injection port to assist in aligning the latch as it is lowered to close the seal.

11. The sealing mechanism claimed in claim 6, wherein the weldment attachment is an annular base ring.

12. The sealing mechanism claimed in claim 11, wherein the base ring and latch are pivotally connected at hinges located on opposing sides of the base ring.

13. The sealing mechanism claimed in claim 12, wherein each hinge is located on the arms substantially close to the channel such that as the latch is levered to seal the injection port, the hinge follows a path around the protrusion in the channel.

14. The sealing mechanism claimed in claim 6, wherein an adapter ring is mountable on an external thread at an inlet of the injection port, and wherein the lever is attachable to the adapter ring and leverable against the adapter ring.

15. The sealing mechanism claimed in claim 14, wherein the adapter ring has an internal thread that cooperates with the external thread.

16. The sealing mechanism of claim 14, wherein the adapter ring is provided with at least one pair of pins extending outwardly of opposing sides on the exterior circumference of the adapter ring, the pins engaging the channels in the latch arms.

17. The sealing mechanism claimed in claim 16, wherein more than one pair of opposing pins are provided on the circumference.

18. The sealing mechanism claimed in claim 16, wherein the adapter is secured in place by radially adjustable grub screws.

19. The sealing mechanism claimed in claim 1, wherein the actuating means is a hydraulic or pneumatic actuator.

20. The sealing mechanism claimed in claim 19, wherein the hydraulic or pneumatic actuator is powered by a source of fluid or compressed air respectively.

21. The sealing mechanism claimed in claim 19, wherein the hydraulic or pneumatic actuator is a ram supported on a frame that is supported against the injection port whereby the ram moves the weldment attachment into sealing.

22. The sealing mechanism claimed in claim 19, wherein the hydraulic or pneumatic actuator has a fluid line with a two-way valve to operate to seal and unseal the sealing mechanism.

23. The sealing mechanism claimed in claim 1, wherein the actuating means is magnetic attraction.

24. The sealing mechanism claimed in claim 23, wherein the magnetic attraction is provided by simple magnets or electromagnets, the magnets being mounted on a frame supported against the injection port.

25. A sealing mechanism for a gas chromatograph machine comprising:
   an annular base mountable at the weldment assembly of a gas chromatograph machine, the base having a passage therethrough for gas communicated to the weldment assembly;
   a lever pivotally connected to the annular base and pivotally attached to an injection port of the gas chromatograph machine, wherein the base is adapted to be seated on top of the injection port and sealed against thereto by pivotally moving the lever to apply a direct force and clamp the base onto the injection port.

26. A sealing mechanism for a gas chromatograph machine comprising:
   an annular base mountable on the inlet weldment assembly of a gas chromatograph machine, the base providing a passage therethrough for gas;
   a latch having two arms pivotally connected on opposing sides on the exterior circumference of the annular base, the arms being provided with hinging means to hingedly attach the latch to a corresponding attachment on an injection port of the machine, the base being mountable on the injection port, wherein the latch is pivotally levered against the injection port to directly clamp the base onto the injection port in sealing engagement and without imparting torsional force on the base.

27. The sealing mechanism claimed in claim 26, wherein the side arms of the latch contain recesses on inner faces thereof that engage with corresponding pins extending from an adapter ring mountable on the injection port.

28. The sealing mechanism as claimed in claim 27, wherein the pins extend outwardly of opposing sides on the exterior circumference of the adapter.

29. The sealing device as claimed in claim 28, wherein more than one pair of opposing pins are provided on the circumference.

30. The sealing mechanism as claimed in claim 27, wherein the adaptor ring threads onto an external thread of the injection port.

31. The sealing mechanism as claimed in claim 30, wherein the adaptor ring is secured in place by radially adjustable grub screws.

32. The sealing mechanism as claimed in claim 27, wherein the recesses are a curved shape such that, during levering, the pins follow a curved path in the recesses that will cause the base to pull down onto the injection port to seal the port.

33. The sealing mechanism as claimed in claim 26, wherein the base and latch are pivotally connected at hinges located on opposing sides of the base.

34. The sealing mechanism as claimed in claim 33, wherein each hinge is located on the arm substantially close to the recess such that as the latch is levered to seal the injection port, the hinge follows a path around the recess.

35. The sealing mechanism as claimed in claim 26, wherein the arms terminate in flanges having cambered edges which provide a cam surface against the injection port to assist in correct movement of the latch as it is lowered to close the seal.

36. The sealing mechanism as claimed in claim 26, wherein the latch has a lever handle.

37. A method of sealing a weldment assembly and an injection port on a gas chromatograph machine including:

mounting a weldment assembly onto the injection port, wherein the weldment assembly includes a latch having two arms and is pivotally connected to opposite sides of the exterior circumference of an annular base, the arms having coupling means for coupling with complementary means located at the injection port in order to mount the latch onto the injection port; and pivotally levering the latch at the coupling to clamp the base down onto the injection port.

38. The method as claimed in claim 37, further including mounting an adapter ring on the injection port, wherein the adaptor ring is provided with pins extending outwardly of its external circumference, the latch arms having recesses that couple with the pins on the adapter.

39. A method of sealing a weldment assembly and an injection port on a gas chromatograph machine including:

mounting a weldment attachment at the weldment assembly, the weldment attachment providing a passage therethrough for gas communicated to the weldment assembly;

actuating an actuating means connected to the weldment attachment, and thereby applying a direct force on the weldment attachment moving it towards the injection port and sealingly clamping the weldment attachment against the injection port, wherein torsional forces are not applied on the weldment attachment by the actuating means.

* * * * *